(12) United States Patent
Kirsch et al.

(10) Patent No.: US 8,463,406 B2
(45) Date of Patent: Jun. 11, 2013

(54) PROBE ELECTRODE PAD AND PROBE ELECTRODE PAD STORAGE BOX

(75) Inventors: Daniel L. Kirsch, Mineral Wells, TX (US); Sai Cheong Chan, West Kowloon (HK)

(73) Assignee: Electromedical Products International, Inc., Mineral Wells, TX (US)

( * ) Notice: Subject to any disclaimer, the term of this patent is extended or adjusted under 35 U.S.C. 154(b) by 0 days.

(21) Appl. No.: 13/247,332

(22) Filed: Sep. 28, 2011

(65) Prior Publication Data

US 2012/0018346 A1 Jan. 26, 2012

Related U.S. Application Data

(63) Continuation of application No. 12/219,878, filed on Jul. 30, 2008, now abandoned.

(60) Provisional application No. 60/935,233, filed on Aug. 1, 2007.

(51) Int. Cl.
*A61N 1/00* (2006.01)
*B65D 85/00* (2006.01)

(52) U.S. Cl.
USPC .......................................... 607/145; 206/701

(58) Field of Classification Search
USPC .......... 607/145, 115, 139–140, 148; 206/570, 206/701; 600/395, 383
See application file for complete search history.

(56) References Cited

U.S. PATENT DOCUMENTS

| | | | |
|---|---|---|---|
| 3,036,726 A | 5/1962 | Wilkins | |
| 3,060,923 A | 10/1962 | Reiner | |
| 3,788,317 A | 1/1974 | McCormick | |
| 4,180,079 A | 12/1979 | Wing | |
| 4,446,870 A | 5/1984 | Wing | |
| 4,488,557 A | 12/1984 | Engel | |
| 4,635,642 A | 1/1987 | Cartmell et al. | |
| 4,796,632 A | 1/1989 | Boyd et al. | |
| 4,890,608 A | 1/1990 | Steer | |
| 5,265,614 A | 11/1993 | Hayakawa et al. | |
| 6,132,378 A | 10/2000 | Marino | |
| 6,400,975 B1 | 6/2002 | McFee | |
| 6,732,648 B1 | 5/2004 | Rogers et al. | |
| 6,839,583 B1 | 1/2005 | Lewandowski et al. | |
| 6,848,581 B2 * | 2/2005 | Cohen .......................... | 206/534 |
| 7,029,446 B2 | 4/2006 | Wendelken et al. | |
| 2003/0134535 A1 | 7/2003 | Martin et al. | |
| 2004/0143286 A1 | 7/2004 | Johnson et al. | |
| 2005/0265900 A1 * | 12/2005 | Gard et al. ................... | 422/100 |
| 2006/0259027 A1 | 11/2006 | Kwan et al. | |

(Continued)

FOREIGN PATENT DOCUMENTS
EP 0206646 12/1986

*Primary Examiner* — Christopher D Koharski
*Assistant Examiner* — Catherine Voorhees
(74) *Attorney, Agent, or Firm* — Welsh Flaxman & Gitler LLC

(57) ABSTRACT

The present invention is directed to a unique, user-friendly, disposable electrode to be used on metallic probes which are used in electromedical devices, such as transcutaneous electrical nerve stimulators (TENS) and microcurrent electrical therapy (MET) devices and other electrical simulators for applying electricity through the skin to the human or animal body. Additionally, the present invention describes a box for the storage and retrieval of the probe.

10 Claims, 6 Drawing Sheets

U.S. PATENT DOCUMENTS

| | | |
|---|---|---|
| 2007/0027524 A1 | 2/2007 | Johnson et al. |
| 2007/0032742 A1 | 2/2007 | Monson et al. |
| 2008/0027345 A1 * | 1/2008 | Kumada et al. ............... 600/544 |
| 2008/0240999 A1 | 10/2008 | Timpson et al. |

* cited by examiner

PROBE ELECTRODE PAD AND PROBE ELECTRODE PAD STORAGE BOX

CROSS-REFERENCED PATENT APPLICATION

This application is a continuation of U.S. patent application Ser. No. 12/219,878 entitled, PROBE ELECTRODE PAD AND PROBE ELECTRODE PAD STORAGE BOX, filed Jul. 30, 2008, now abandoned, which claims the benefit of U.S. Provisional Patent Application Ser. No. 60/935,233, filed Aug. 1, 2007.

FIELD OF THE INVENTION

The present invention is directed to electrode pads applied to an electrical probe as well as a container for storing the electrode pads.

BACKGROUND OF THE INVENTION

With the utilization of transcutaneous electrical nerve stimulators (TENS) and micro current electrical therapy (MET), as well as other modalities of electromedicine it is necessary to apply electrical current of a particular waveform into the body. A probe terminating in a metallic head is often used to deliver the electrical current from a treatment device to the body. Between the probe head and the skin, it is desirable to use an electrode pad with the characteristics shown in TABLE I to serve the purposes described therein.

TABLE I

| Purposes to be served by the electrode pad | Desirable characteristics of the electrode |
| --- | --- |
| 1 To be meant for one-time use for hygiene reasons. | Inexpensive. Easy to be put on and taken off the probe head. |
| 2 To cushion skin from the unpleasant physical contact of a cold and hard metallic probe head. | Made of soft materials which fully encompass the probe head and which are safe and comfortable to stay in touch with skin for a long period of time. |
| 3 To ensure electrical contact between skin and the probe head with the introduction of the electrode. | Ability to absorb and retain a conductive solution. |
| 4 To remain in position for the entire treatment period, despite the possibility that the probe will be moved around to different locations on the body and pressed and twisted in all possible directions on each location. | Attachment to the probe head is secured despite frequent and rigorous traction forces on the electrode from all possible directions. |
| 5 To bear the logo of the manufacturer of the electrode pad. | Ability to be printed upon with water-insoluble ink. |

Prior art electrical probes and pads inserted on the end of the probes are described in U.S. Pat. Nos. 4,180,079 and 4,446,870, both issued to Wing. Both of these patents describe the use of a probe directly connected to a metallic housing or case adapted to be held in the hand of the user and applied to the surface of a body. The probe utilizes a conventional electrical jack having a hollow interior. An ear swab in the form of a cotton wad is attached to a rigid stem inserted into the hollow cylinder of the electrical jack. During the operation of the probe, it may be necessary to remove the ear swab. This is accomplished by pulling on the ear swab to remove the swab as well as the rigid stem from the hollow interior of the electrical jack. In some cases, if the swab has been removed from the rigid stem, a needle or the like must be used to expel the rigid stem from the hollow interior of the electrical jack, at which time, a new swab including its rigid stem is inserted into the hollow interior of the electrical jack.

As can be appreciated, it will be required by a doctor, medical technician, or the patients themselves to physically touch the ear swab prior to and when the rigid stem attached to the pad would be inserted into the electrical jack, as well as when the swab would be removed. Even if the aforementioned individuals would be wearing gloves, the placement of the swab into the probe is not optimally hygienic. Additionally, the removal of the swab from the probe would be quite difficult, particularly if the swab would be broken off from its rigid stem.

SUMMARY OF THE INVENTION

The problems of the prior art electrode swabs or pads are overcome by the present invention which includes a probe electrode pad specifically designed to be easily inserted onto a ball-shaped probe head as well as to be removed from the probe head. Even though this is the case, the probe electrode pad would still be firmly attached to the probe head, despite frequent and rigorous traction forces on it from all possible directions.

According to another feature of the invention, the probe electrode pad is specially designed to fully encompass the probe head, and to cushion the human or animal skin from the unpleasant physical contact of a cold and hard metallic probe head.

According to another feature of the invention, the probe electrode pad is specially designed to be made of raw materials which are inexpensive, able to absorb and retain conductive solutions, printable with a water-insoluble ink and proven to be safe and comfortable to remain in contact with the human skin for a long period of time.

According to still another feature of the present invention, a storage box is provided to store the probe electrode pads prior to use and to easily allow each individual pad to be attached to the probe body, without the probe head and the probe electrode pad being touched by the fingers and hands of doctors, medical technicians or the patients themselves.

BRIEF DESCRIPTION OF THE DRAWINGS

In the following, the present invention is illustrated by way of example and not limiting with reference to the accompanying drawings in which.

Understanding that these drawings depict only typical embodiments of the invention are not to be construed to limited scope, the invention will be described in detail below.

DETAILED DESCRIPTION OF THE PRESENT INVENTION

Figure 1:
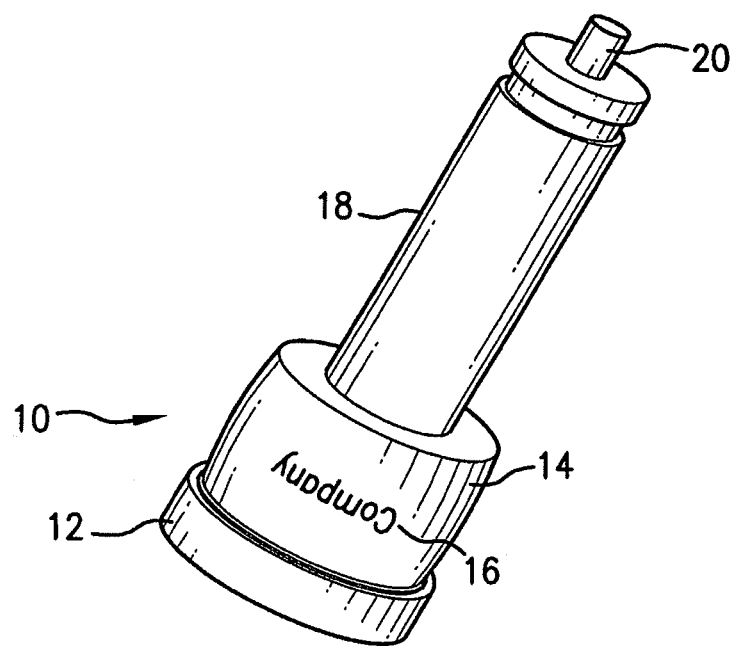
FIG. 1 is a perspective view of a probe electrode pad attached to a ball-shape probe head.
Figure 2:
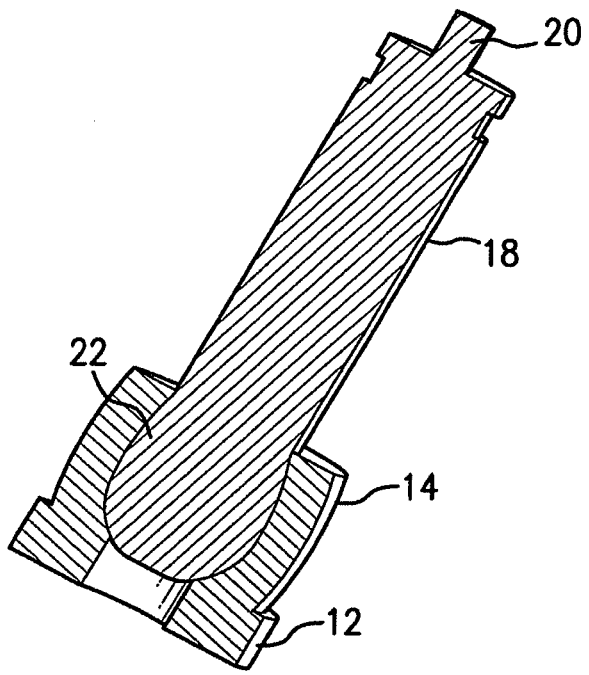
FIG. 2 is a cross-sectional view of the probe electrode pad attached to the ball-shaped probe head.

As illustrated with respect to FIGS. 1 and 2, a metallic electrode probe 18 is provided with a ball-shaped probe head 22 to be inserted and confined within a probe electrode pad 10. The probe electrode pad 10 includes a pad 12 constructed from felt or cotton such as natural or synthetic cotton wool widely used on bandages which has been proven to be safe and comfortable when it remains in contact with the human skin for a relatively long period of time. Additionally, this type of material is relatively inexpensive. Furthermore, it is important that this material readily absorb and retain a conductive solution which is to be applied onto the pad 12 before any treatment begins. A sleeve 14 is provided, into which the head 22 will be inserted.

The electrode probe 18 can be used in conjunction with a plurality of electromedical devices, such as transcutaneous electrical nerve stimulators (TENS), microcurrent electrical therapy (MET), to list a few. The probe 18 is connected to one of these devices utilizing a metallic connector rod 20.

Figure 3:
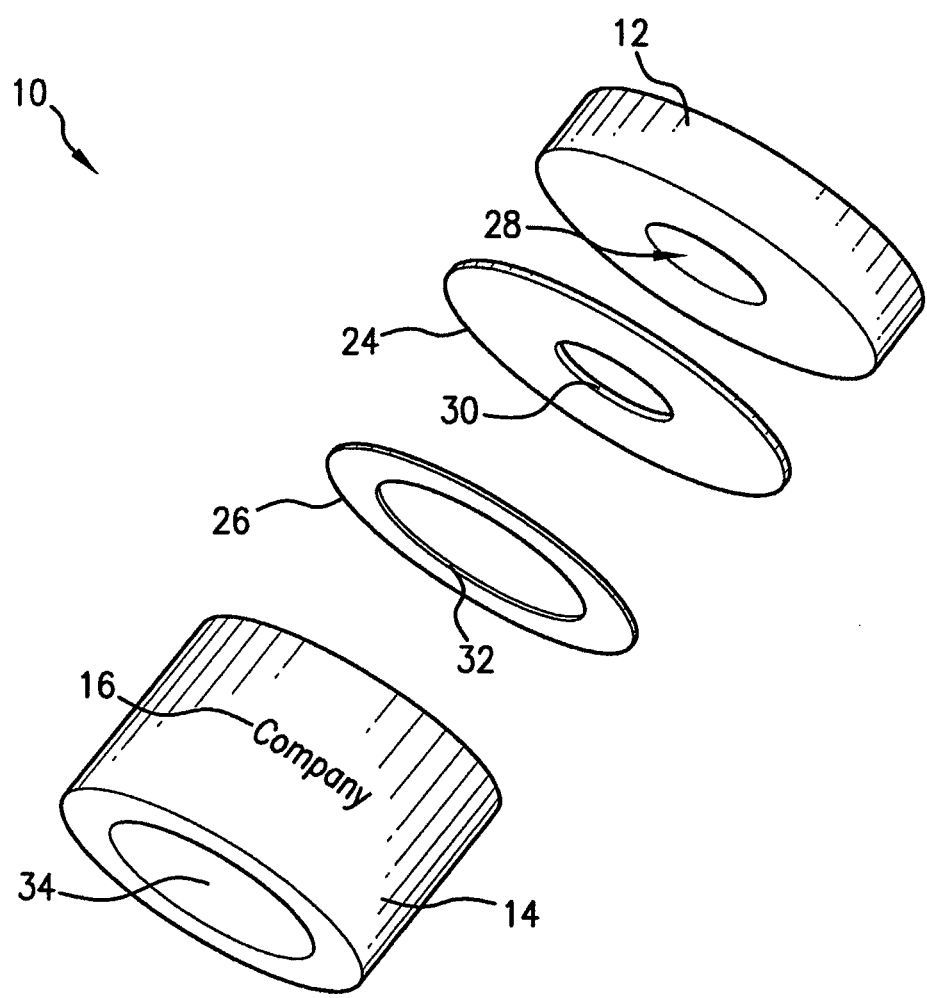
FIG. 3 is an exploded perspective view of the probe electrode pad.
Figure 4:
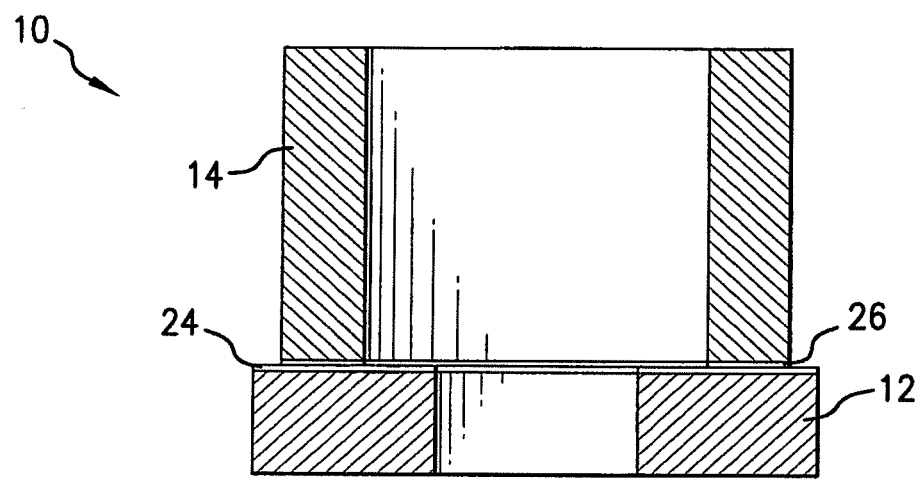
FIG. 4 is a vertical cross-section of the electrode probe pad shown in FIG. 3.
Figure 5:
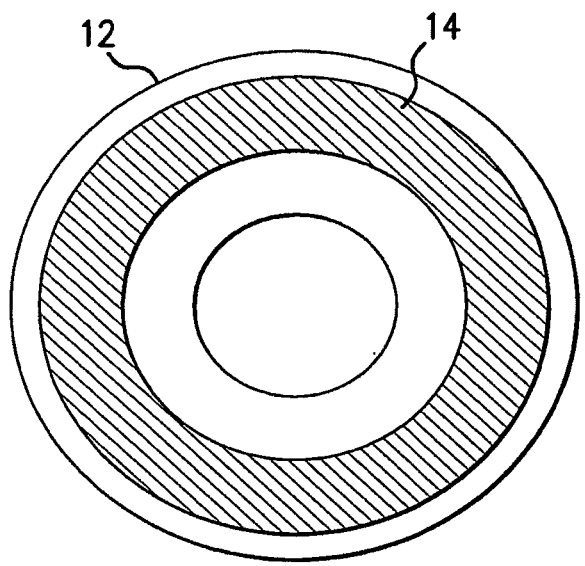
FIG. 5 is a horizontal cross-section of the electrode probe pad shown in FIG. 3.

The electrode probe pad 10 is shown in more detail in FIGS. 3, 4 and 5. As illustrated in these figures, the pad 12 is connected to the sleeve 14 through the use of double-sided adhesive tapes 24 and 26 to firmly attach the pad 12 to the sleeve 14. The pad 12 is provided with a central hole 28 extending completely through the middle of the pad 12. Double-sided tape 24 is provided with a central hole 30 therethrough, the diameter of which is equal to or larger than the diameter of the central hole 28. The double-sided tape 26 is provided with a hole 32 therethrough and the sleeve 14 is provided with a central hole 34 extending from one side of the sleeve to the other side of the sleeve. The diameter of the hole 32 of the double-sided tape 26 is approximately equal to or is slightly less than the diameter of the hole 34 of the sleeve 14. What is important, is that the double-sided tape 26 be affixed to the end of the sleeve 14 facing the double-sided tape 24 which is attached to the side of the pad 12 closest to the sleeve 14.

In a preferred embodiment, the pad 12 is shaped like a donut and has an outer diameter of approximately 10 millimeters optimized to cover an acupuncture or trigger point. The height of the pad 12 is approximately 2.2 millimeters to allow the appropriate substance of the pad 12 to absorb and retain sufficient conductive solution for a treatment period. The hole 28 extending through the pad 12 is approximately 3.5 millimeters in diameter to allow the conductive solution in the pad 12 to make electrical contact with the probe head 22 which in turn is provided within the sleeve 14. An example of the conductive solution would be NDC 36-331015.

The sleeve 14 is constructed from a soft and elastic ethylene vinyl acetate (EVA). The sleeve 14 has a length of approximately 6 millimeters so that the entire probe head 22 would be completely contained therein. The central hole 34 of the sleeve 14 has a diameter of approximately 6 millimeters which is specifically designed to be slightly smaller than the 7 millimeter diameter of a standard ball-shaped probe head 22, allowing the sleeve 14 to be gripped firmly on the probe head 22. The outer diameter of the sleeve 14 is approximately 9 millimeters to give itself an optimum amount of substance to insure the solid nature of the sleeve 14 and yet to allow printing 16 such as a company logo or other information to be printed thereon. Therefore, the material of the sleeve 14 must also be elastic to readily allow the probe head 22 to be slipped onto and out of the sleeve 14.

When the sleeve 14 is to be slid onto the probe head, the interior of the sleeve would grip the probe head 22 firmly and the entire probe electrode head assembly is able to withstand frequent and rigorous traction forces from all possible directions. The approximate dimensions of the pad 12, the double-sided tapes 24 and 26 as well as the sleeve 14 are shown in FIGS. 4 and 5 wherein the approximate length of each of the tapes is 0.1 millimeter. However, as can be appreciated, these dimensions are relative based upon the type and size of the probe head 22. The use of a smaller probe head 22 would generally reduce the dimensions of the probe electrode pad 10 and a larger size probe head 22 would relatively increase the dimensions of the probe electrode pad 10.

Figure 6:
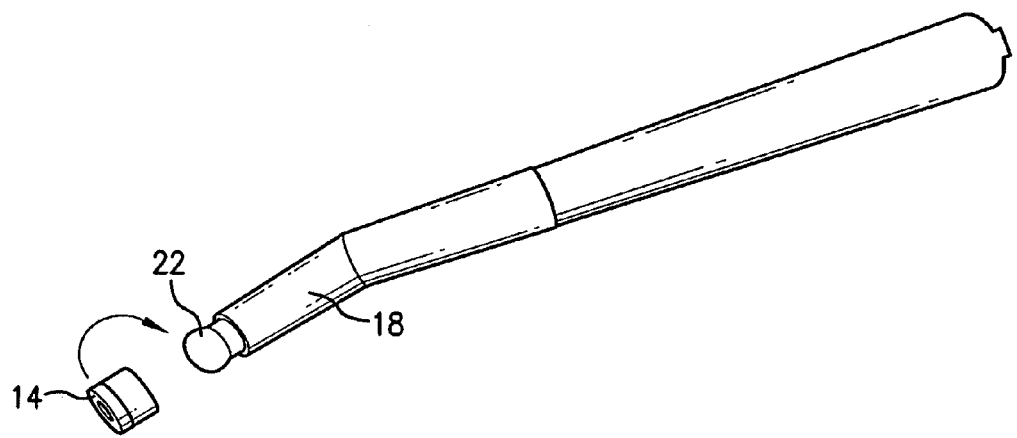
FIG. 6 is a perspective view of a typical probe head and electrode combination.

FIG. 6 illustrates the probe electrode pad 14-probe assembly 18 prior to the probe head 22 being inserted into the hole 34 of the sleeve 14. As previously described, one of the deficiencies of the prior art was the fact that it was difficult to hygienically apply a probe electrode pad to the head of a probe. Additionally, once applied to the probe head, it was often difficult to easily remove the probe electrode pad from the probe and to replace it with another pad.

Figure 7:
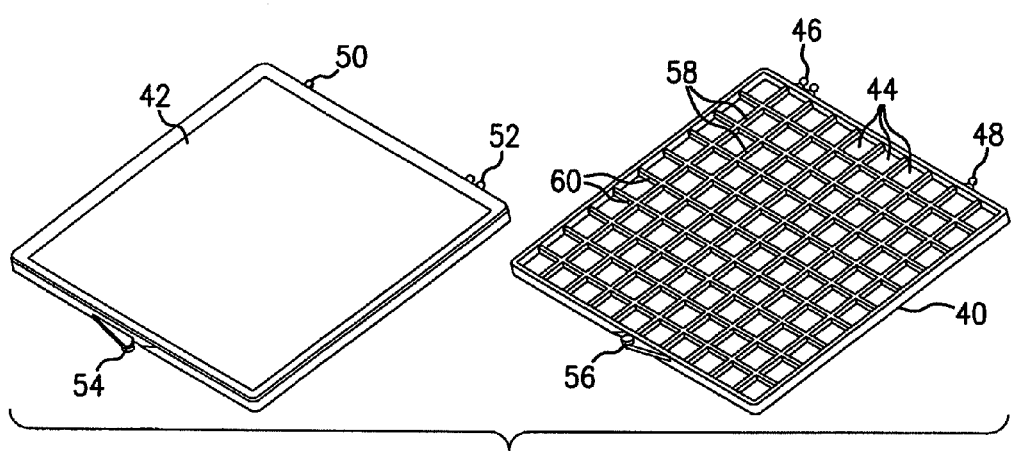
FIG. 7 is a perspective drawing of the top and bottom of the probe electrode storage box of the probe electrode storage box.
Figure 8:
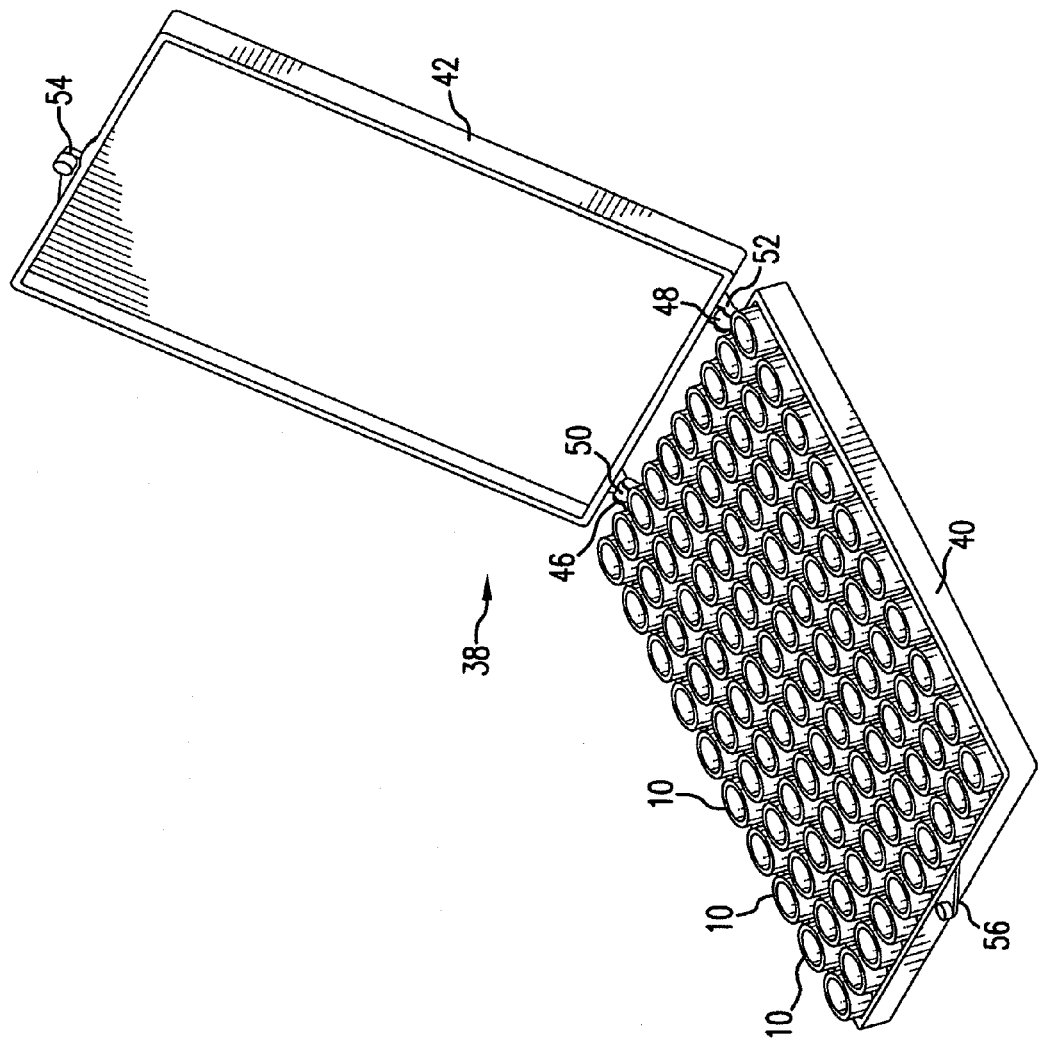
FIG. 8 is a perspective view of the probe electrode storage box.

The deficiency of the prior art relating to the application of the probe electrode pad 10 to the probe head 22 of a probe 18 is alleviated utilizing the storage box 38 shown in FIGS. 7 and 8. Although the storage box 38 shown in FIG. 8 illustrates the storage of 100 probe electrode pads 10, it can be appreciated that any number of pads can be stored therein. What is important, is that the base 40 of the storage box 38 be provided with a plurality of square compartments 44, each of which would contain a single probe electrode pad 10 with the pad 12 facing the bottom of each of the wells 44 and the sleeve 14 facing outwardly from each of the compartments 44 provided on the base 40 of the box 38. Each of the probe electrode pads 10 would remain in its respective compartments 44 due in part to the fact that the outer diameter of the pad 12 is greater than the outer diameter of the sleeve 14 as previously described. Each pad is held in its respective compartment 44 through the use of a friction fit between the walls of the compartment 44 and the pad 12 itself, as well as due to the circular membrane configuration of the pad 10 which is provided within its respective square compartment 44.

The square compartments are created by providing a plurality of vertical wall segments 58 and a plurality of horizontal wall segments 60, all of which are extending from one side of the base 40 to its opposite side. Since all of the wall components 58 are parallel to one another and all of the wall components 60 are parallel to one another, the plurality of square compartments wells 44 are created. Each compartment would hold probe electrode pad 10 therein with the hole 34 of the sleeve 14 facing up so that each of the probe electrode pads 10 may be directly picked up from the box by inserting the probe head 22 into hole 34 of the sleeve 14. The storage box shown in FIGS. 7 and 8 can be constructed from many solid materials. However, it is found that an injection molded material of plastic resin would work particularly well. As previously indicated, the exact dimensions of the box 38 and the number of compartments 44 therein are not crucial to the present invention. It is noted that a box 38 can be created with 100 square compartments 44 provided within a box having a dimension of 112 millimeters v. 112 millimeters v. 12 millimeters. These particular dimensions when used with the dimensions of the probe electrode pad 10 illustrated in FIGS. 4 and 5 would allow the four walls of each of the compartments to press lightly upon the perimeter of the pad 12 to hold the probe electrode pad 10 in position even if the box is held upside down and the lid 42 of the box is open. As shown in FIG. 8, the height of each of the electrode pads 10 is greater than the height of the upstanding exterior walls of the storage box 38. Additionally, since the plurality of square walled compartments 44 are provided within the storage box 38. the height of each of the probe electrode pads 10 is greater than the height of the square walled compartments 44.

The lid 42 is hingedly attached to the base 40 using a pair of hinges employing a ball 48 affixed to one side of the base 40 and a ball 50 affixed to one side of the lid 42. Holding devices 46 and 52 are affixed respectively to one side of the base 40 and one side of the lid 42. Therefore, in constructing the box 38, ball 48 would be snapped into the holding device 52 and ball 50 would be snapped into the holding device 46, thereby creating a hinged joint between the lid 42 and the base 40 of the storage box 38. As can be appreciated, the type of hinge joint which is created is not important to the practice of the present invention. For example, both of the balls 48 and 50 could be fixedly attached to either the base 40 or the lid 42 and the holding devices 46 and 52 would then be attached to the opposite lid 42 or base 40.

The storage box 38 is provided with a locking device including a ridge 54 attached to one end of the lid 42 and a ridge 56 attached to the base 40, both ridges cooperating with one another when the lid 42 is closed upon the base 40 thereby locking the lid 42 to the base 40.

In operation, to affix one of the probe electrode pads 10 to the ball-shaped head 22 of probe 18, the ball-shaped probe head would be inserted into the opening 34 of the sleeve 14 such that the head 18 is fully trapped within the sleeve 14. At this point, the probe 18 would be lifted from the storage box 38 with the probe electrode pad 10 being affixed thereto.

The conductive solution would then be applied to the surface of the pad 12 which would then flow to the probe head 22. The probe head 22 is then applied to the skin of the individual. If a new pad 10 is to be applied to the probe head 22, the old pad would be removed by a doctor or medical technician gripping the old pad 10 with their hands or an appropriate tool, and then pulling the pad 10 away from the probe head 22, thereby removing the pad 10. At this point, a new pad 10 can be applied to the probe 22 as previously explained.

While the foregoing is directed to a preferred embodiment of the present invention, other and further embodiments of the invention may be devised without departing from the basic scope thereof. For example, as previously indicated, the dimensions of the probe electrode pad as illustrated and described can be changed based upon the size of the probe body. Additionally, the size and shape of the storage box as well as a number of compartments provided therein can also change depending on various circumstances.

What is claimed is:

1. A probe electrode pad and storage box combination for use with an electrode probe having a ball-shaped head comprising:

a plurality of probe electrode pads, each probe electrode pad comprising a cylindrical absorbent pad and a cylindrical sleeve affixed to said cylindrical absorbent pad, said cylindrical absorbent pad constructed from a flexible material, said cylindrical absorbent pad having an outer diameter A, and a first central hole, said first central hole having a diameter M, said cylindrical sleeve having an outer diameter B, with B less than A, said cylindrical sleeve provided with a second central hole having a diameter O greater than diameter M;

a storage box provided with a base and a plurality of square walled compartments, each of said square walled compartments storing one of said plurality of probe electrode pads with each of said cylindrical absorbent pads held in place with a friction fit with the walls of each respective walled compartment, the height of each of said square walled compartments being less than the height of said absorbent pad; and wherein the electrode probe is provided with a ball-shaped head having a diameter greater than M, and when the electrode probe is inserted into said second central hole of one of said cylindrical sleeves, a single one of said electrode probe pads is removed from said storage box.

2. The probe electrode pad and storage box combination in accordance with claim 1, wherein the height of said probe electrode pad is greater than the height of each of said upstanding exterior walls.

3. The probe electrode pad in accordance with claim 1, wherein said absorbent pad is provided with a second central hole.

4. The probe electrode pad in accordance with claim 1, wherein said absorbent pad is affixed to said sleeve utilizing an adhesive.

5. The probe electrode pad in accordance with claim 3, wherein said absorbent pad is affixed to said sleeve utilizing an adhesive.

6. The probe electrode pad in accordance with claim 4, wherein said adhesive comprises first and second double-sided adhesive tape.

7. The probe electrode pad in accordance with claim 5, wherein said adhesive comprises first and second double-sided adhesive tape.

8. The probe electrode pad in accordance with claim 7, wherein said first and second double-sided tapes are provided with third and fourth central holes, respectively.

9. The probe electrode pad in accordance with claim 1, wherein said sleeve is constructed from ethylene vinyl acetate.

10. The probe electrode pad and storage box combination in accordance with claim 1, further including a lid hingedly attached to said base of said storage box.

* * * * *